United States Patent
Ahle et al.

(10) Patent No.: US 6,855,139 B2
(45) Date of Patent: Feb. 15, 2005

(54) AUTOMATED TISSUE WELDING SYSTEM AND METHOD

(75) Inventors: Karen Marie Ahle, Quantico, VA (US); Brooke C. Basinger, Scottsdale, AZ (US); Jason De Camp, El Paso, TX (US); Kenton W. Gregory, 3737 SW. Council Crest Dr., Portland, OR (US) 97201; Elizabeth Whitney Johansen, Littleton, CO (US); Benjamin Charles Martin, Los Gatos, CA (US); Cyndia A. Sweet, Hillsboro, OR (US)

(73) Assignees: Providence Health System-Oregon, Portland, OR (US); Kenton W. Gregory, Portland, OR (US)

(*) Notice: Subject to any disclaimer, the term of this patent is extended or adjusted under 35 U.S.C. 154(b) by 0 days.

(21) Appl. No.: 10/132,079

(22) Filed: Apr. 24, 2002

(65) Prior Publication Data

US 2003/0204182 A1 Oct. 30, 2003

Related U.S. Application Data

(60) Provisional application No. 60/286,231, filed on Apr. 24, 2001.

(51) Int. Cl.[7] .............................................. A61B 18/04
(52) U.S. Cl. ............................... 606/8; 128/898; 606/2
(58) Field of Search ....................... 606/2–16; 128/898

(56) References Cited

U.S. PATENT DOCUMENTS 5,571,216 A * 11/1996 Anderson ................... 128/898
5,651,783 A * 7/1997 Reynard ........................ 606/4
6,099,522 A * 8/2000 Knopp et al. ................ 606/10
6,129,722 A * 10/2000 Ruiz ............................. 606/5
6,551,306 B1 * 4/2003 Carriazo ........................ 606/5
2001/0051800 A1 * 12/2001 Eugeny et al. ................ 606/8

OTHER PUBLICATIONS

Kagan et al., "Welding with Light", *Machine Design*, pp. 79–82 (Aug. 3, 2000).
Zacks, "Welding Wounds", *Technology Review*, pp. 73–76 (Nov./Dec. 1998).
Marx, "Applications of High–power Diode Lasers", *European Report*, pp. 114–116 (Sep. 1998).
Kincade, "Diode Lasers Proliferate at BiOS Symposium", *LaserFocusWorld*, 2 pages (Mar. 1995).
Kincade, "Feedback Device Should Improve Tissue Welding", *LaserFocusWorld*, 3 pages (Jul. 1995).
Dixon, "Fibers Turn Free–space Beams Into Guided Waves", *LaserFocusWorld*, 5 pages (Nov. 1997).
Newman, "Stronger Laser Tissue Welds Being Developed", *Urology Times*, p. 6 (Dec. 1996).
Remote Control, *HD: Hospital Development*, p. 34 (Mar. 2000).

* cited by examiner

*Primary Examiner*—Lee S Cohen
*Assistant Examiner*—Henry M Johnson, III
(74) *Attorney, Agent, or Firm*—Marger Johnson & McCollom PC

(57) ABSTRACT

An automated energy irradiator guidance system is disclosed which reduces the potential for human error and improves the consistency and repeatability of tissue welding techniques. The system includes a mapper, a patternizer, an energy director and can additionally include an energy regulator. An interface is included, allowing pattern creation, selection and editing by a user. The system further provides control of energy irradiator parameters for use in tissue welding.

14 Claims, 6 Drawing Sheets

AUTOMATED TISSUE WELDING SYSTEM AND METHOD

CROSS REFERENCE TO RELATED APPLICATIONS

This application claims priority from U.S. Provisional Application No. 60/286,231, filed on Apr. 24, 2001, which is incorporated by reference.

STATEMENT OF GOVERNMENT RIGHTS

This invention was made with U.S. Government support under Grant Number DAMD17-96-6006, awarded by the Army Medical Research and Materiel Command. The U.S. Government may have certain rights in the invention.

This research was funded in part by Grant Nos. DAMD17-96-1-6006 and DAMD17-98-1-8654. The U.S. government may have certain rights in the present disclosure.

BACKGROUND OF THE INVENTION

The present invention is related to the field of tissue welding, and more specifically to a device and method for automating tissue welding in a living body.

Tissue closure is most commonly performed using sutures, which are inexpensive, reliable, and readily available. Unfortunately, sutures cause additional tissue damage during their placement and tying. Sutures also result in the introduction of a foreign material into the body, increasing the risk for further damage or rejection. Moreover, sutures do not necessarily result in a water tight seal and may require a long healing time.

The placement of sutures involves a complicated set of movements that may be difficult of impossible in microsurgical or minimally invasive applications. Other mechanical methods such as staples or clips have the advantage of being uniform but the disadvantage of inflexibility, and the same basic limitations apply.

Laser tissue welding is the procedure of using focused laser energy to bond tissues together. The absorbed energy results in a molecular alteration of the affected tissue and causes bonds to form between neighboring tissues. Laser soldering is a method of improving tissue welding by introducing a proteinaceous solder material between the tissue or other surfaces to be joined prior to exposure to the laser. Soldering is beneficial for its ability to enhance bond strength, lessen collateral damage, and enlarge the parameter window for a successful bond. The solder is able to do this by holding the tissues together creating a larger bonding surface area, sometimes by as much as two degrees of magnitude.

Laser tissue welding has been used successfully in nerve, skin, and arterial applications. The technique offers significant advantages for securing and sealing skin grafts, repairing solid-tissue organ damage, minimizing laceration trauma, and closing surgical incisions. A major advantage of tissue welding is the instant tissue healing and sealing that it offers, which allows for a quicker return to functional recovery.

Tissue welding typically uses an 800 nm-range laser in conjunction with a chromophore (e.g., indocyanine green (ICG)) to essentially heat, denature and fuse together skin and organ tissues. In a representative method, a solution of albumin and ICG is applied to a wound site. While skin, blood and other bodily tissues have low absorption coefficients in the infrared and near-infrared range, ICG has an absorbance peak at 800 nm. The thermal energy emitted by the laser is thereby confined to the ICG, adjacent albumin applied at the weld site, and the immediately surrounding area. During irradiation, collagen fibers in the tissue deform under thermal stress and form new couplings at the molecular level.

Current tissue welding techniques are highly dependent on the individual skill and technique of the operating surgeon. Laser tissue welding processes require the surgeon to determine the appropriate dose of laser energy, then manually apply irradiation by directly manipulating an optical fiber handpiece. Accurate determination of optimal laser parameters is difficult in this system. Furthermore, manual control of laser positioning and movement can, and often does, lead to under or overexposure of tissues to laser energy, which can cause failed welds and tissue death, respectively.

The success of tissue welding techniques can vary greatly due to manual laser control. The variation in technique among surgeons makes accurate research difficult, if not impossible, and the lack of standardized irradiation patterns and dosages only adds to the inconsistency of tissue welding procedural success. For laser welding to reach its full potential, it must become a more consistent and repeatable process.

DETAILED DESCRIPTION OF PREFERRED EMBODIMENT(S)

An automated energy irradiator guidance system is disclosed which reduces the potential for human error and improves the consistency and repeatability of tissue welding techniques. The system includes a clinically useable energy irradiator guidance system with an interface allowing pattern creation, selection and editing by a user. The system further includes a surface overlay display, and control of energy irradiator parameters for use in tissue welding.

Figure 1:
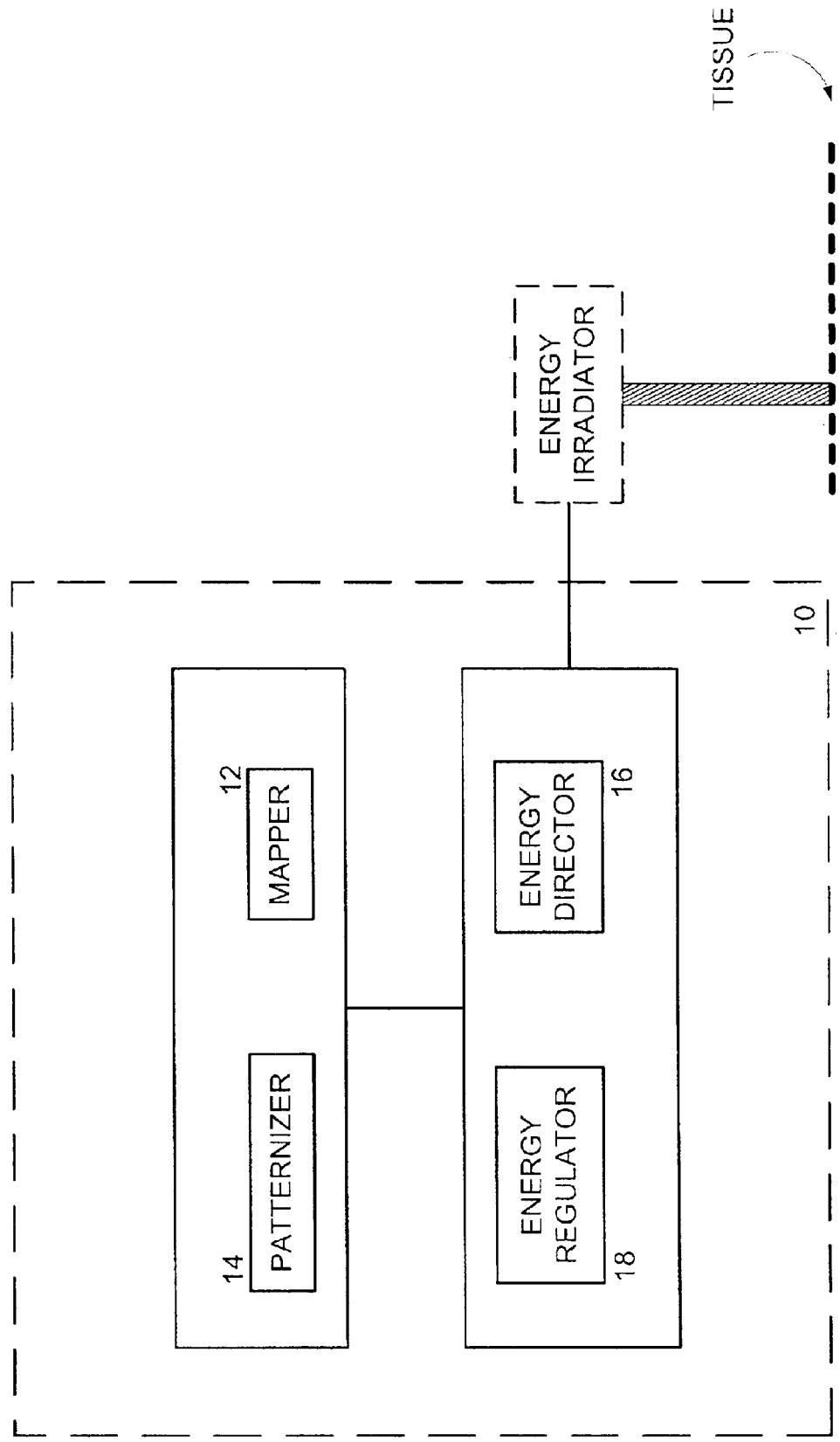
FIG. 1 is a block diagram of one embodiment of an automated tissue welding system.

The system can be used to perform tissue welding at a target site in an organism. As shown in FIG. 1, the system 10 includes a mapper 12, a patternizer 14, an energy director 16 and can additionally include an energy regulator 18.

The energy irradiator (FIG. 1) typically is structured to deliver energy suitable for use in tissue welding; as used in tissue welding, the energy irradiator usually comprises an energy transmitter coupled to a energy source. Tissue welding typically involves localized heat generation by delivering energy to the target site. Light energy from an 800 nm laser is discussed herein; however, those of ordinary skill in the art will appreciate that other forms of energy can be efficaciously employed without departing from the essential principles of the present disclosure.

The mapper 12 is operative to generate a three-dimensional target site map of a target site. The target site on the tissue can be either two- or three-dimensional, although in most cases it will be the latter. In a preferred embodiment, the mapper is operative to generate a topographic target site map of the target site.

Physically, the weld site mapper 12 can include several different components, such as scanners, amplifiers, a power supply, circuit board, an internal computer driver card, and a variety of connecting cables.

The patternizer 14 is operative to synchronize an irradiating pattern with the target site map. In a preferred embodiment, the patternizer is operative to synchronize a two-dimensional irradiating pattern with a three-dimensional target site map. Such synchronization allows the user to implement a variety of irradiating patterns on the target site, regardless of the latter's topography.

The irradiating pattern (FIG. 5) can be a predetermined irradiating pattern. Alternatively, the irradiating pattern can be created by the user, either by combining predetermined patterns or by drawing an irradiating pattern on a display screen. The pattern typically consists of a plurality of irradiation targets, which can be correlated with an equivalent plurality of target loci at the weld site.

The energy director 16 is configured to substantially automatically direct the energy to the target site in the organism in accordance with the irradiating pattern. The energy director can act upon the energy irradiator directly or indirectly. For example, the energy director can comprise one or more motors configured to physically position the energy irradiator to thereby direct irradiated energy to a welding target locus. The director can be configured to automatically direct the energy irradiator in the X-axis and Y-axis, or in the X-axis, Y-axis and Z-axis.

In an indirect energy directing scheme, the energy director can comprise mirrors or other structure structured to direct the energy irradiated from the energy irradiator to the desired welding target locus. In an example in which a laser energy irradiator is employed, the energy director 16 can comprise one or more mirrors. The mirrors can be manipulated to deliver treatment to the target area, with the laser parameters selected and in the pattern chosen by the user.

The system described above can further comprise an energy regulator 18 adapted to regulate energy from the energy irradiator. In one embodiment, the energy regulator is adapted to cause the energy irradiator to deliver a selected amount of energy to an irradiation locus within the target site.

Alternatively, the energy regulator 18 is adapted to cause the energy irradiator to deliver selected amounts of energy to a plurality of irradiation loci within the target site. In another alternative embodiment, the energy regulator is adapted to cause the energy irradiator to deliver a selected amount of energy to each of a plurality of irradiation loci within the target site.

The energy regulator 18 can be an energy positioner configured to determine an energy irradiator position in the X-axis and Y-axis. Alternatively, the energy positioner can be configured to determine an energy irradiator position in the X-axis, Y-axis and Z-axis.

Figure 2:
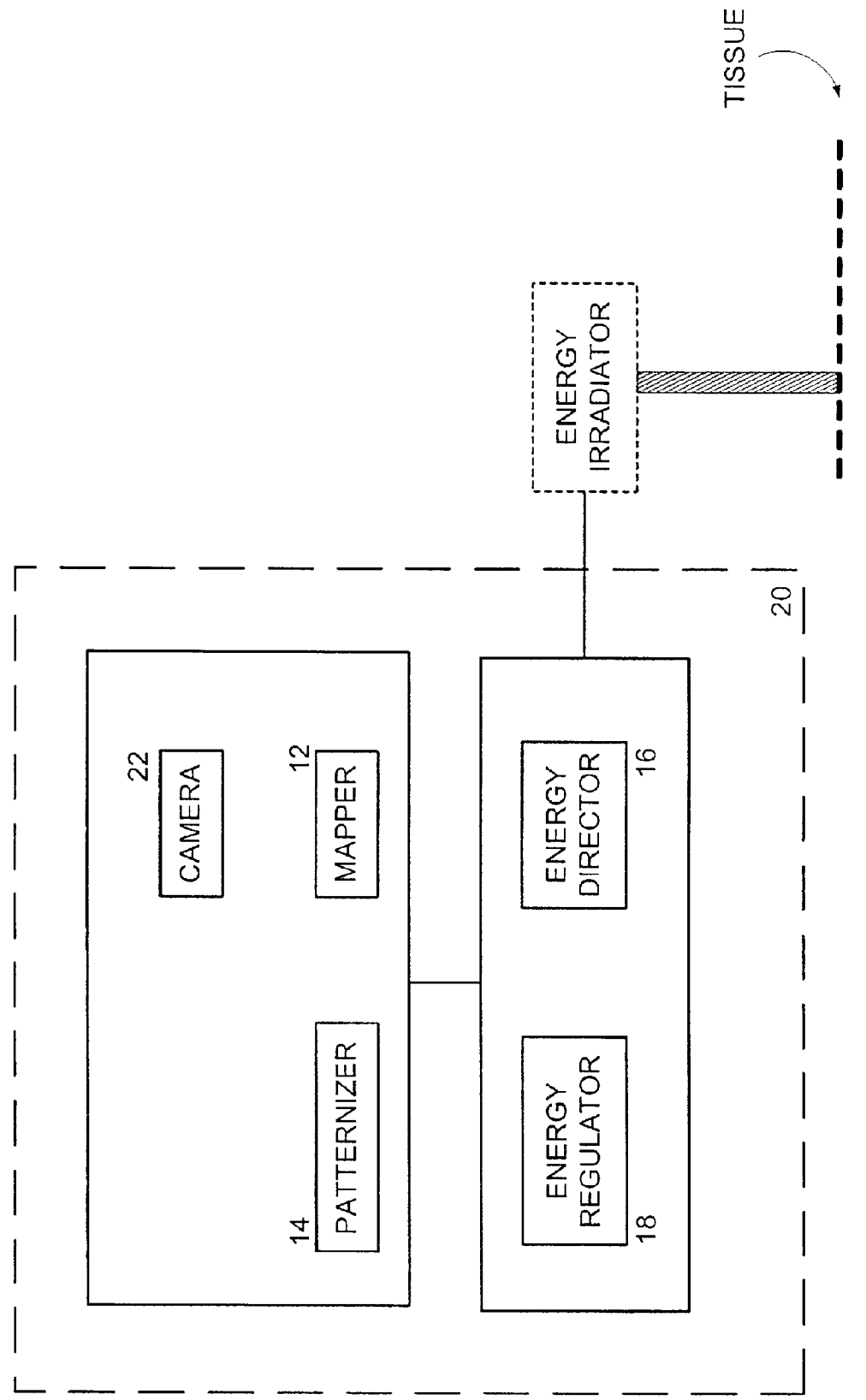
FIGS. 2–3 are alternative embodiments of the system of FIG. 1.

The system 20 shown in FIG. 2 further comprises a camera 22 adapted to output a site image of a targeted tissue weld site. When so equipped, the mapper 12 is operative to generate a three-dimensional target site map from the site image outputted from the camera 22.

The energy regulator 18 can further be operative to correct for irradiating variables to deliver a substantially controlled irradiation dose to the weld site. Such irradiating variables include, for example, energy spot size and distance from the energy transmitter to a target point within the weld site.

Figure 3:
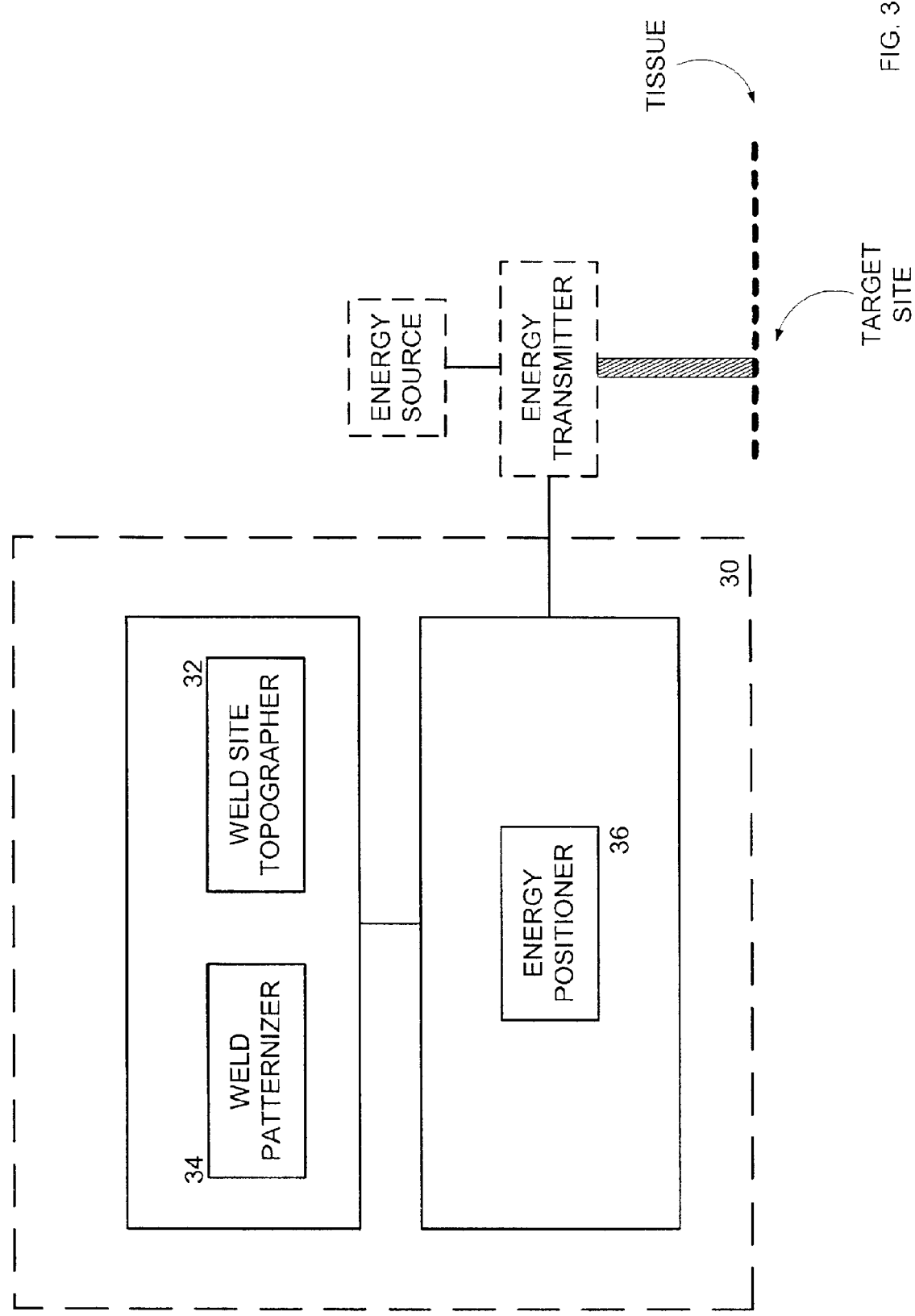

A more simplified embodiment of a tissue welding system 30 is shown in FIG. 3. As discussed above, the weld site topographer 32 is operative to generating a topographical image of the target site.

The weld patternizer 34 is operative to synchronize an irradiating pattern with a two-dimensional or a three-dimensional target site map. The irradiating pattern can also be either two-dimensional or three-dimensional.

A method for automatically directing energy to a target site on a tissue of a living body begins by generating a topographical target site image. The system is capable of topographically mapping a tissue site having a three-dimensional character, although two-dimensional tissue welding sites can also be used.

An irradiation pattern is correlated with the topographical target site image. The irradiation patterns, discussed above, can consist of modifiable predetermined patterns or a custom pattern created by the user.

Once the irradiation pattern is selected and correlated with the topographic image of the target site, irradiation energy is automatically introduced to the target site in the living body in accordance with the irradiation pattern. The system controls the delivery of energy to provide a selected dose to the target loci within the tissue welding site. System control of the energy, both as to strength, duration and position, improves the quality of the tissue welding compared to manual techniques.

Figure 4:
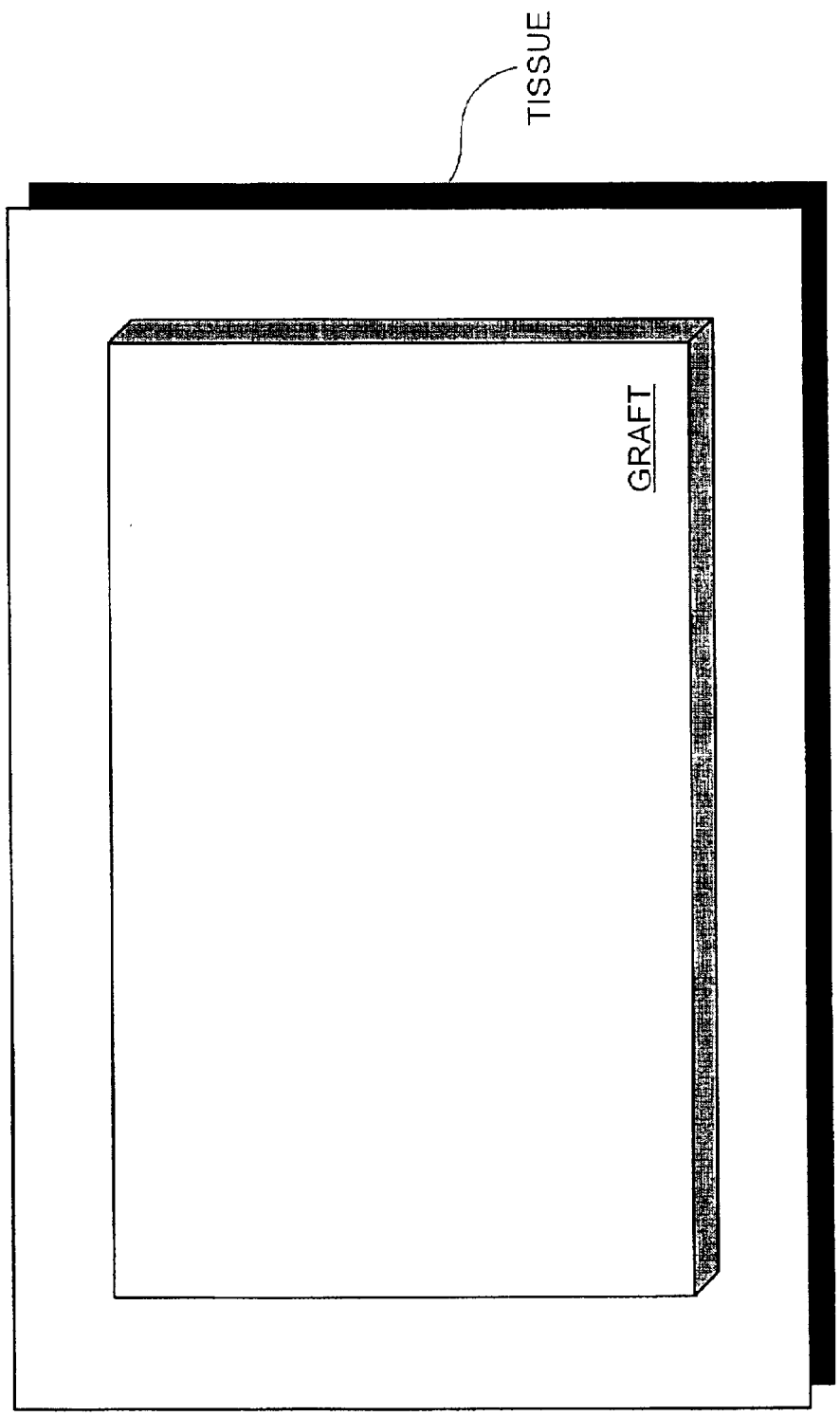
FIGS. 4–5 show a tissue welding site, wherein a graft is to be attached via tissue welding.
Figure 5:
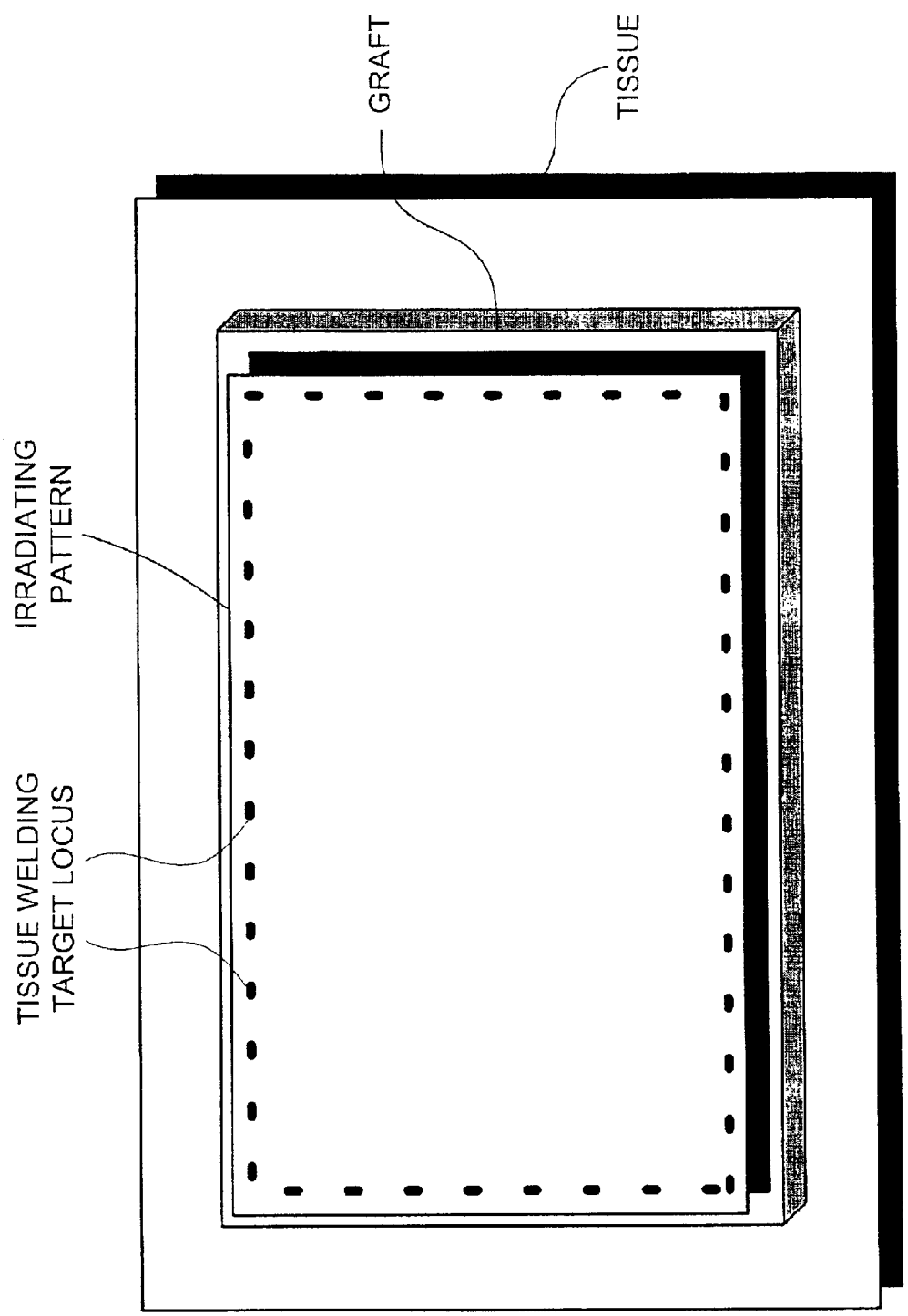

Energy can be automatically directed to a target site on a tissue of a living body to weld together native tissue of the living body, as well as to secure a graft to the tissue (FIGS. 4–5).

In operation, a user must properly prepare the system. Preparation generally includes proper placement of the device over the target area as well as powering up all equipment involved. This stage will not be discussed in detail at this point because it is not crucial to the design of the laser guidance system. It will, however, be assumed that this has been completed and the system is ready to be used.

Most user control over the system will be done through computer interaction. In one design, an image of the weld site can be displayed on, e.g., a computer monitor. The displayed image can be optical or thermal, according to the type of energy used and the user's preference.

The patternizer is configured to provide a plurality of templates (in this case, laser irradiation patterns, such as in FIG. 5) that can be overlaid on top of the weld image. A laser pattern can be resized or altered to better fit the application. It also is possible, in some embodiments, for the user to manually draw a pattern on the display, or to use a previous pattern from memory. If possible, other parameters may be controlled, including laser speed, delay time at each target locus, the number of desired cycles through the chosen pattern, and so on.

Figure 6:
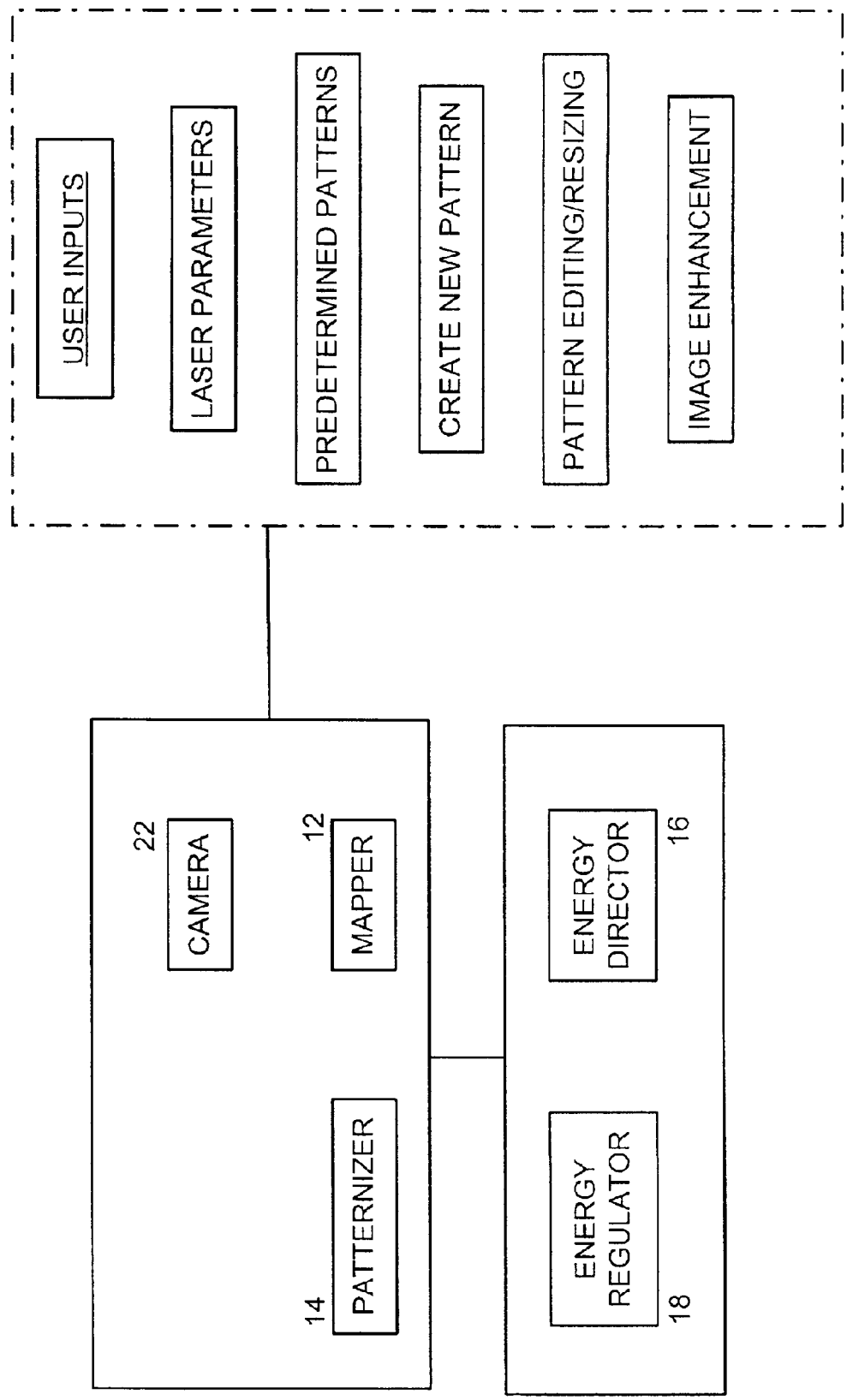
FIG. 6 is a block diagram of a system as disclosed herein, showing representative user inputs.

Laser parameters can also be controlled or adjusted (FIG. 6). For example, the system can allow manipulation of laser power, pulse width, frequency, and other parameters. These parameters typically can all be manually configured on the laser itself, providing both flexibility and a redundant feature for safety. User inputs to the system can be broken down into: pattern editing; creating; selecting; resizing; setting laser parameters; and manual image enhancement control.

Once the laser pattern has been determined and all laser parameters are set to the desired level, the system is ready to begin tissue welding. The user instructs the system to begin, and the system will operate the laser to irradiate the target weld site according to the selected irradiating pattern.

The weld site image input first is enhanced and its edges detected, in order to establish a general pattern shape. This information is then displayed to the user for optional adjustment in a graphics editor. Finally, an irradiating pattern will be decomposed into vector format and converted to a scanner control signal.

A separate function is the laser parameter control, which accepts user input and communicates control signals to control the laser. The basic outputs of the system are a scanner control signal and a laser control signal.

The optics for a laser tissue welding system include all necessary mirrors and lenses, as well as any protective windows that the laser passes through. The present system contemplates two mirrors, a protective window and a plurality of lenses.

The system can use a lens or series of lenses to expand and collimate the beam to a larger spot size before it enters the mirror assembly, thus reducing the intensity that is applied to the surface of the mirrors. The difficulty in this option is that any beam with a low enough intensity not to damage the mirrors may have too low an intensity to effectively weld tissues together. It is then necessary to focus the beam back down to a smaller beam size before it reaches the target tissue.

Beam focusing is preferably accomplished by using the initial set of lenses to produce a very long focal distance that will reach the mirrors while maintaining a "medium" spot size, yet have a smaller spot size and thus a larger intensity by the time it reaches the tissue. This approach is calculated to produce a higher light intensity at the weld site than at the mirror surface.

It is theoretically impossible to focus the beam to an exact point; instead the beam will reach a minimum waist size before diverging. At longer focal lengths, that minimum achievable waist size becomes larger and larger, potentially reducing the beam's intensity at the irradiation site beyond the intensity necessary for effective welding.

A primary consideration of the camera is depth of field, i.e., the depth within which the camera must remain focused. To calculate the depth of field, both the furthest and closest points to the camera must be considered. Equation (4) relates these focal points to depth of field:

$$\text{further distance} - \text{closest distance} = \text{depth of field} \quad (4)$$

For the present system, it is impracticable to directly center the camera on the path of the laser, because the laser beam will be obstructed. Hence, the other critical factor in determining depth of field is the displacement between the center of the target area and the placement of the camera. In equation (5), depth of field depends on the length, L, of the side of the square target area, the perpendicular distance, d, between the camera and the target area, and the displacement, x, between the center of the target area and the camera:

$$[(0.5L+d)^2+(0.5L)^2+d^2]^{0.5}-d=\text{depth of field} \quad (5)$$

Note that the depth of field quantity determined with a specific camera position in mind is no longer valid if the camera is moved to a position a different distance from the tissue. In this case, a new calculation must be performed. To ensure that the system will accommodate the most difficult depth of field case, calculations were performed using equation (5) with two different target area sizes (10×10 cm and 20×20 cm) and two different distances between the camera and target area (10 cm and 30 cm) (Table 2).

TABLE 2

Sample Camera Depth of Field Calculation

| L (cm) | d (cm) | x (cm) | depth of field (cm) |
|--------|--------|--------|---------------------|
| 10     | 10     | 2      | 3.2                 |
| 20     | 10     | 2      | 8.6                 |
| 10     | 30     | 2      | 1.2                 |
| 20     | 30     | 2      | 3.8                 |

The laser tissue welding system herein described can weld a flat, square graft to a 10×10 cm piece of flat tissue from a distance of 10–30 cm. Optics are included that will support the selected energy irradiator, e.g., an 800 nm, pulsed diode laser of beam diameter ranging between 0.2 and 0.8 mm, maximum beam intensity approximately 10 kW/cm$^2$.

A person skilled in the art will be able to practice the present invention in view of the description present in this document, which is to be taken as a whole. Numerous details have been set forth in order to provide a more thorough understanding of the invention. In other instances, well-known features have not been described in detail in order not to obscure unnecessarily the invention.

While the invention has been disclosed in its preferred form, the specific embodiments thereof as disclosed and illustrated herein are not to be considered in a limiting sense. Indeed, it should be readily apparent to those skilled in the art in view of the present description that the invention can be modified in numerous ways. The inventor regards the subject matter of the invention to include all combinations and sub-combinations of the various elements, features, functions and/or properties disclosed herein.

What is claimed is:

1. A method for automatically directing energy to a target site on a tissue of a living body, comprising:
   generating a topographical target site image;
   correlating an irradiation pattern with the topographical target site image; and
   automatically introducing irradiation energy to the target site in the living body in accordance with the irradiation pattern to weld together native tissue of the living body.

2. The method of claim 1 wherein energy is automatically directed to a target site on a tissue of a living body to secure a graft to the tissue.

3. The method of claim 1 wherein correlating an irradiation pattern with the topographical target site image comprises correlating a two-dimensional irradiation pattern with the topographical target site image.

4. The method of claim 1 wherein correlating an irradiation pattern with the topographical target site image comprises correlating a plurality of irradiation pattern loci in the irradiation pattern with a corresponding plurality of target loci in the topographical target site image.

5. The method of claim 1 wherein automatically introducing irradiation energy comprises correcting for irradiating variables to deliver a selected irradiation dose to each target locus in the topographical target site image.

6. The method of claim 5 wherein automatically introducing irradiation energy includes correcting for an energy spot size of an energy irradiator.

7. The method of claim 5 wherein automatically introducing irradiation energy includes correcting for a distance from an energy transmitter to a target locus in the target site.

8. A method for welding tissue at a weld site in a patient, comprising:
   generating a topographical image of the weld site;

correlating an irradiation pattern with the topographical image; and automatically introducing irradiation energy to the weld site in the patient in accordance with the irradiation pattern.

9. The method of claim 8 wherein correlating an irradiation pattern with the topographical image comprises correlating a two-dimensional irradiation pattern with the topographical target site image.

10. The method of claim 8 wherein correlating an irradiation pattern with the topographical image comprises correlating a plurality of irradiation pattern loci in the irradiation pattern with a corresponding plurality of target loci in the topographical target site image.

11. The method of claim 8 wherein automatically introducing irradiation energy comprises correcting for irradiating variables to deliver a selected irradiation dose to each target locus in the topographical image.

12. The method of claim 11 wherein automatically introducing irradiation energy includes correcting for an energy spot size of an energy transmitter.

13. The method of claim 11 wherein automatically introducing irradiation energy includes correcting for a distance from an energy transmitter to a target locus in the weld site.

14. The method of claim 8 wherein energy is automatically directed to a target site on a tissue of a living body to secure a graft to the tissue.

* * * * *